(12) United States Patent
Patel et al.

(10) Patent No.: US 8,979,866 B2
(45) Date of Patent: Mar. 17, 2015

(54) SURGICAL TOOL

(75) Inventors: Vinay D. Patel, Memphis, TN (US);
Shannon D. Cummings, Hernando, MS (US)

(73) Assignee: Wright Medical Technology, Inc., Memphis, TN (US)

( * ) Notice: Subject to any disclaimer, the term of this patent is extended or adjusted under 35 U.S.C. 154(b) by 266 days.

(21) Appl. No.: 13/561,839

(22) Filed: Jul. 30, 2012

(65) Prior Publication Data

US 2014/0031828 A1  Jan. 30, 2014

(51) Int. Cl.
*A61B 17/02* (2006.01)
*A61B 17/70* (2006.01)
*A61B 17/68* (2006.01)

(52) U.S. Cl.
CPC ......... *A61B 17/025* (2013.01); *A61B 2017/681* (2013.01); *A61B 17/0206* (2013.01); *A61B 17/7077* (2013.01); *A61B 2017/0256* (2013.01)
USPC ........................................... 606/105; 606/90

(58) Field of Classification Search
USPC .......... 600/218, 219, 222, 226; 606/86 R, 90, 606/105; 81/318, 319, 324, 328, 329, 331, 81/336, 337
See application file for complete search history.

(56) References Cited

U.S. PATENT DOCUMENTS

| | | | | |
|---|---|---|---|---|
| 3,564,694 A | * | 2/1971 | Millheister | 29/229 |
| 4,896,661 A | * | 1/1990 | Bogert et al. | 606/86 R |
| 4,898,161 A | | 2/1990 | Grundei | |
| 5,674,244 A | * | 10/1997 | Mathys | 606/208 |
| 6,551,316 B1 | * | 4/2003 | Rinner et al. | 606/57 |
| 6,635,072 B1 | * | 10/2003 | Ramamurti et al. | 606/208 |
| D488,229 S | | 4/2004 | Rinner et al. | |
| 6,716,218 B2 | | 4/2004 | Holmes et al. | |
| 7,081,118 B2 | | 7/2006 | Weber et al. | |
| 2002/0123754 A1 | * | 9/2002 | Holmes et al. | 606/105 |
| 2010/0004695 A1 | * | 1/2010 | Stad et al. | 606/86 A |
| 2014/0031828 A1 | * | 1/2014 | Patel et al. | 606/90 |

* cited by examiner

*Primary Examiner* — Michael T Schaper
*Assistant Examiner* — Amy Sipp
(74) *Attorney, Agent, or Firm* — Duane Morris LLP

(57) ABSTRACT

A surgical tool includes a pair of pivotally coupled operating handles and working distal ends connected thereto configured to engage bone fixation elements. A toothed ratchet member is arranged across the handles and includes a first and second tooth rack. The first tooth rack includes a plurality of teeth angled in a first direction and the second tooth rack includes a plurality of teeth angled in a second direction. The ratchet member is rotatable with respect to the handles to selectively present the first or second tooth rack to a pawl disposed on one of the handles. The handles are operable for closing or spreading movement via selective engagement of the pawl with the first or second tooth rack, which correspondingly closes or spreads the working distal ends. A method for operating the tool is also disclosed.

8 Claims, 11 Drawing Sheets

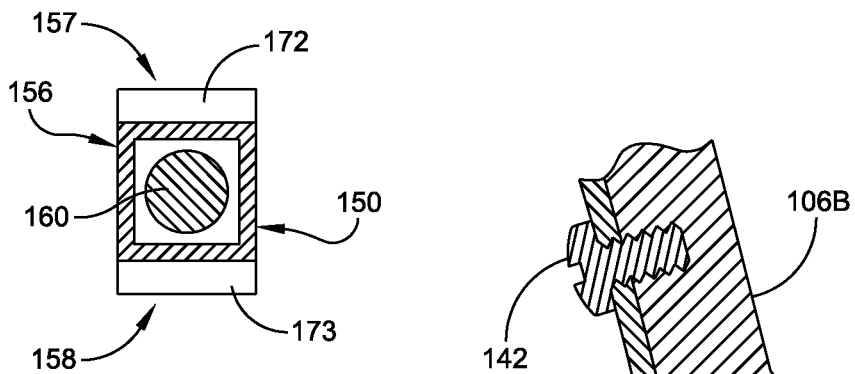
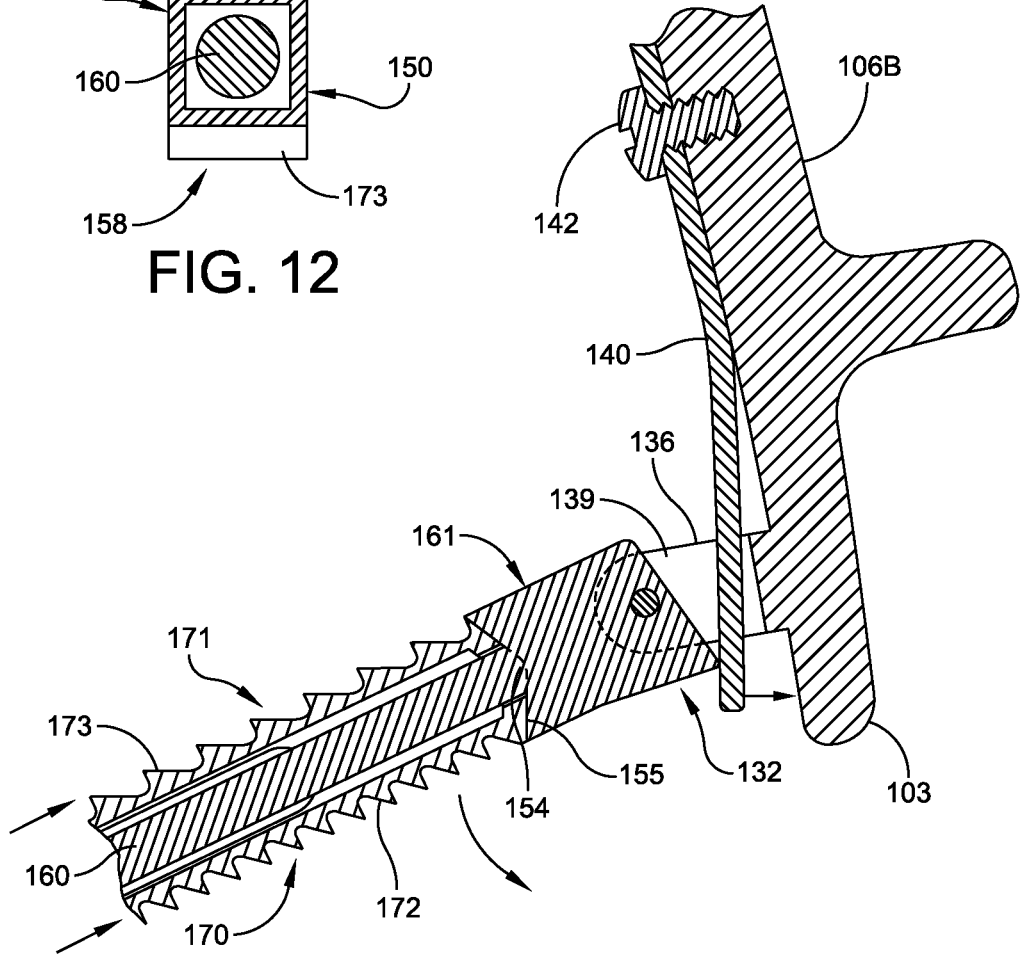
FIG. 12
FIG. 11

SURGICAL TOOL

FIELD OF DISCLOSURE

The present disclosure relates to surgical devices, and more particularly to a surgical tool and related method useable for orthopedic procedures including joint repair involving distraction and compression.

BACKGROUND

Surgical joint repair procedures sometimes involve the distraction or spreading of bone joints to temporarily hold the joint open which allows the surgeon to gain access to opposing joint surfaces and anatomical features such as cartilage lying therebetween. In some cases, this involves first inserting K-wires (Kirschner wires) through the bones adjacent to the joint. The loose wire ends are then attached to working ends of a surgical tool such as a distractor which operates in scissor-like fashion. The distractor is operated to distract and hold the joint open during completion of whatever surgical repair is needed. When the surgeon is finished, the K-wires are detached from the distractor which is removed. A different tool such as a compressor is then attached to the K-wire ends and the joint is compressed or closed using the tool. This tool switchover may be cumbersome and increases the surgical procedure time.

Accordingly, improved surgical tools and method are desirable for joint distraction and compression.

SUMMARY

A surgical tool is disclosed which in one embodiment advantageously includes both a distraction operating configuration or mode and a compression operating configuration or mode. The tool is transformable between both operating configurations in-situ during the surgical joint repair or other procedure without detachment from the patient or bone fixation elements such as K-wires.

According to one embodiment, a surgical tool includes a body including a distal working portion and a proximal operating portion pivotally coupled to the working portion. The working portion includes a pair of elongated working members each having a distal end configured for engaging a fixation element securable to a bone segment. The working members are movably coupled together and configured for motion in an opening or spreading distraction direction and a closing compression direction with respect to each other. The operating portion includes a pair of elongated handles pivotally coupled together and configured for opening and closing movement with respect to each other. The operating portion is configured so that moving the handles apart in an opening direction moves the working members together in the closing compression direction, and moving the handles together in a closing direction handles moves the working members apart in the opening distraction direction. An elongated toothed ratchet member is arranged across the handles and pivotally coupled to one of the handles. The ratchet member is engageable with a pawl disposed on the other handle. The ratchet member is rotatable, with respect to the handles, between two different operating positions. When the ratchet member is in a first operating position engaged with the pawl, the handles are movable in the closing direction and prevented from movement in the opening direction by the ratchet bar, and when the ratchet mechanism is in a second operating position engaged with the pawl, the handles are movable in the opening direction and prevented from movement in the closing direction by the ratchet bar. Through rotation of the ratchet member, it is possible to change operating configurations of the tool from a compression tool to a distraction tool, and vice versa.

According to another embodiment, a surgical tool for distraction and compression operation includes a first handle having a proximal and distal ends, a second handle having proximal and distal ends, the first handle being pivotally coupled to the second handle for relative opening and closing movement, a first lateral arm pivotally coupled to the first handle, and a second lateral arm pivotally coupled to the second handle. The first and second lateral arms are movably coupled together for relative opening and closing movement. The tool further includes a pawl disposed on the second handle and an elongated ratchet member arranged across the handles and pivotally coupled to the first handle. The ratchet member is rotatable with respect to the handles. The ratchet member has a first tooth rack comprising a plurality of teeth angled in a first direction and a second gear rack comprising a plurality of teeth angled in a second direction opposite the first direction. The first and second tooth racks are selectively and alternatingly engageable with the pawl by rotating the ratchet member.

According to another aspect of the present disclosure, an exemplary method for operating the surgical tool is provided. In one embodiment, the method includes: providing a tool comprising a pair of handles pivotally coupled for grasping, a pair of working members operably coupled to the handles and configured to engage a fixation element securable to a bone segment, and a toothed ratchet member arranged between the handles and being configured to engage a pawl disposed on one handle and having a first end pivotally coupled to one of the handles; engaging a first tooth rack disposed on a first side of the ratchet member with the pawl; rotating the ratchet member; and engaging a second tooth rack disposed on a second side of the ratchet member with the pawl. In one embodiment, the first tooth rack and second tooth rack are arranged 180 degrees apart on the ratchet member.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 11 is an enlarged cross-section side view thereof showing pivoting of the ratchet member with respect to the handle;

FIG. 12 is a cross-sectional view taken through the ratchet member along line 12-12 in FIG. 5;

DETAILED DESCRIPTION

Figure 1:
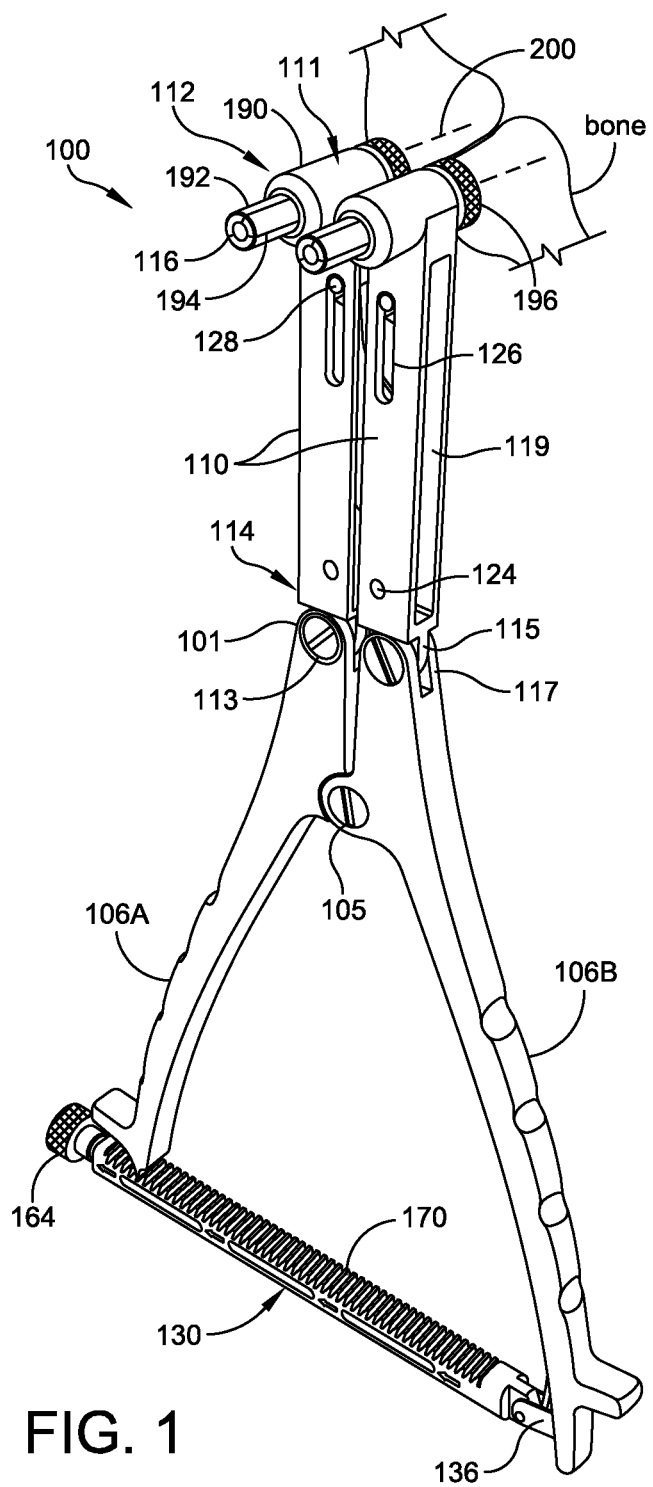
FIG. 1 is a front perspective view of one exemplary embodiment of an improved surgical tool configured for compression and distraction operation.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship.

FIGS. 1-4 show an embodiment of a surgical tool 100 according to the present disclosure that is operable to perform both distraction and compression of a bone joint via a movable operating mode switch. Tool 100 has a body defining a longitudinal tool axis LA and generally includes a distal working portion 102, a proximal operating portion 104 movably coupled to the working portion, and the operating mode control switch disposed on the operating portion. In one embodiment, the operating mode switch is an elongated toothed ratchet member 130. Ratchet member 130 is configured and operable to control and limit/restrict the movement of the operating portion 104 as further described herein.

Working portion 102 includes a pair of laterally arranged and adjacent working members such as axially elongated arms 110. Arms 110 each include a working distal end 112 configured to engage a bone-fastener such as a K-wire and an opposite proximal end 114 (see FIGS. 1-4.) Arms 110 are configured and structured to act as structural members capable of applying a force to an object such as without limitation a bone-fastener that may be secured to a bone segment. In one embodiment, arms 110 may have a generally rectilinear configuration overall (best shown in FIG. 1) with a square or rectangular cross-sectional shape, and in some embodiments define an axially extending internal passageway 119. Other suitable configurations of arms 110 may alternatively be provided and are contemplated.

In one potential application, tool 100 may be used in conjunction with bone joint repair surgery and is operable for distraction of the joint (i.e. spreading) and compression of the joint in two different user selectable operating modes, as further described herein. With continuing reference to FIGS. 1-4, working distal ends 112 of arms 110 are configured to engage a bone fixation element as noted above such as without limitation a bone fastener or K-wire (Kirschner wire) in some embodiments which is securable to a bone segment. In one embodiment, distal ends 112 include a hole 116 configured to temporarily receive therethrough and engage a portion of a K-wire. In one embodiment, distal ends 112 include cylindrical locking members 111 such as collets which define holes 116 and are operable to apply a clamping force on the K-wire or bone fastener. Locking members 111 are operable to tighten against a K-wire or shaft of another bone fastener.

Figure 13:
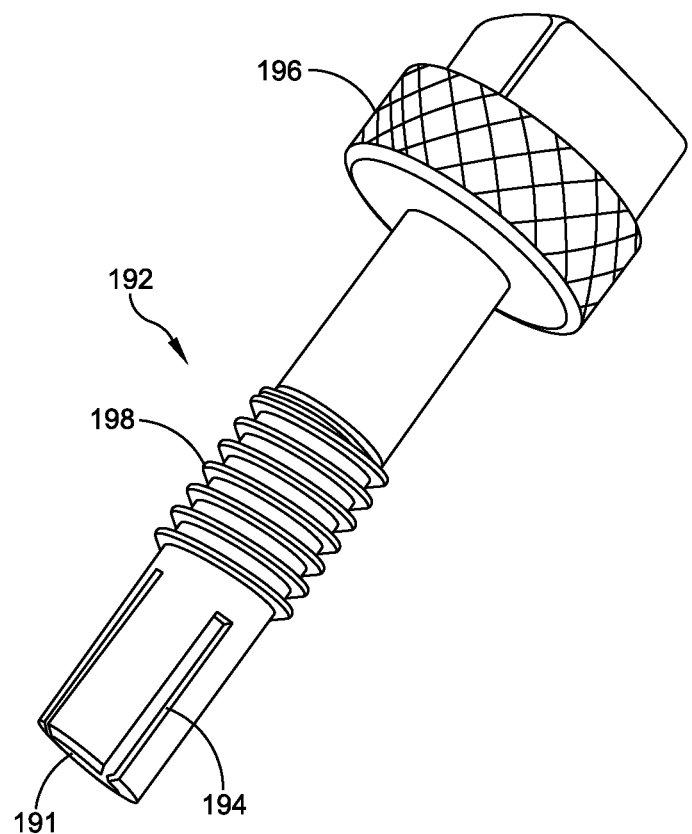
FIG. 13 is a perspective view of a collet sleeve useable to form clamping ends in the surgical tool of FIG. 1.

In one embodiment, as shown in FIGS. 1 and 13, locking members 111 include an outer hollow cylindrical collar 190 and inner hollow sleeve 192 configured and dimensioned for insertion into the collar. Sleeve 192 includes a distal end 191 and proximal end 196 configured for grasping by the fingers and/or a tool such as a wrench, socket, or insertable key. In one embodiment, as shown in FIG. 13, proximal end 196 may include a knurled or other textured surface configured as a knob and/or a tool engagement element configured to engage a tool for rotating sleeve 192. In some embodiments, tool engagement element can be configured as a square (shown) or other shaped polygonal protrusion (e.g. hexagon, decagon, octagon, etc.) or a suitably configured polygonal recess or socket (e.g. hexagon, square, etc.) to engage a complementary configured tool or key insertable therein. Inner sleeve 192 further includes a threaded portion 198 configured to engage a mating threaded portion inside a passageway extending completely through outer collar 190 (not shown). Distal end 191 includes a plurality of radially spaced apart kerfs or slits 194 extending axially from the distal end towards the proximal end 196 for a distance to a point terminating before threaded portion 198. As commonly found in collet-type clamping devices or chucks, the distal end 191 portion of sleeve 192 adjacent at least part of the slits 194 is tapered and flared slightly outwards to function as a chuck for clamping a K-wire or other bone fastener. In operation, the K-wires are inserted through inner sleeve 192. As the inner sleeve 192 is inserted and screwed into the outer collar 190 via the knurled surface or tooling protrusion, the outwardly flared tapered distal end 191 adjacent slots 194 engages the inside surfaces of the passageway in outer collar and are compressed inwards by the interaction thereby pinching around and clamping the K-wire.

In alternative embodiments, distal ends 112 of lateral arms 110 may each be a non-clamping design which is configured to merely engage, but not rigidly clamp the K-wires in holes 116. The K-wires would be merely inserted through plain holes 116 which can be drilled or otherwise formed into the ends 112.

Figure 3:
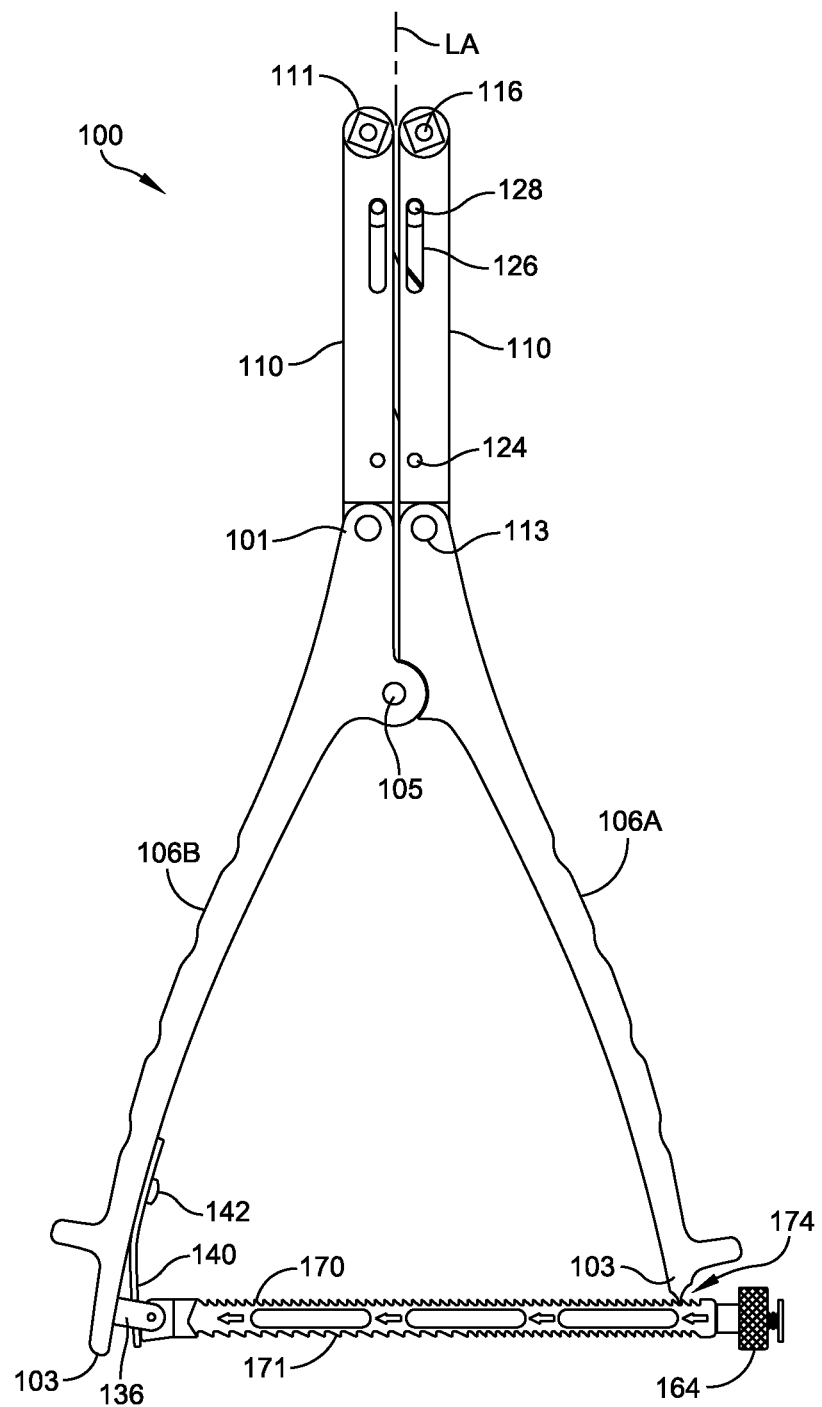
FIG. 3 is a rear elevation view thereof.
Figure 4:
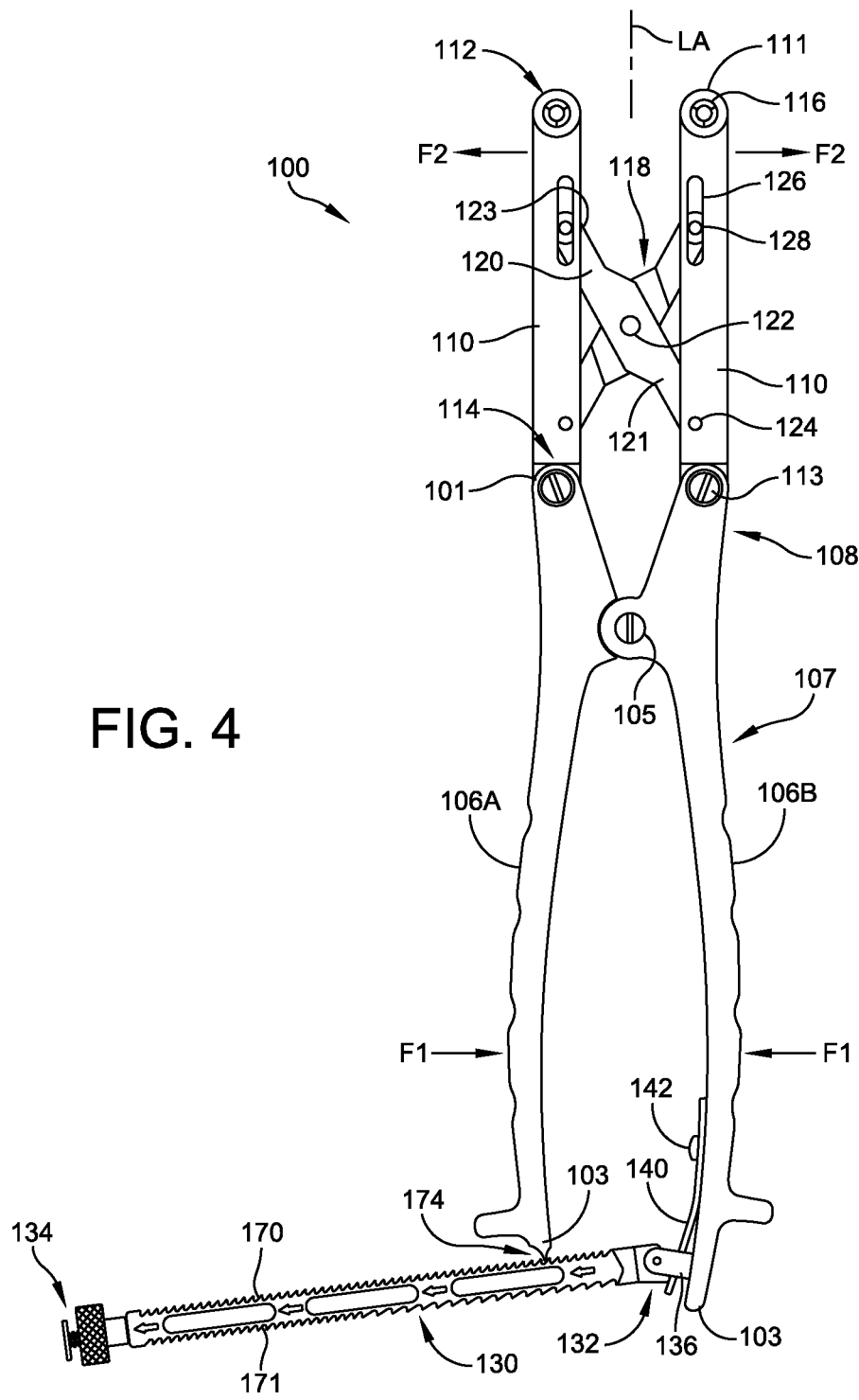
FIG. 4 is front elevation view thereof showing working members in an open position handles in a closed position.

As best shown in FIG. 4, working portion 102 is configured so that arms 110 are movably coupled together for movement in unison. In one embodiment, this is provided by an openable/closeable motion control brace 118 comprised of a pair of cross supports 120 which are pivotally connected together proximate to their midpoints by pivot pin 122 which defines a pivot point. Control brace 118 is configured such that the motion of one arm 110 controls the motion of the interconnected opposing arm 110 via movement of and interaction with the brace. Each cross support 120 has a proximal end 121 which is pivotally pinned by pin 124 to arm 110 and a distal end 123 which is slidably engaged with arm 110 via a guide protrusion 128 that is received in an axially elongated slot 126 as shown in FIGS. 1-4. In one embodiment, protrusion 128 is cylindrical in shape with a circular cross section. End 121 is fixed in axial position with respect to arm 110 albeit pivotally movable about pin 124. Opposing end 123 is axially movable in a longitudinal direction along arm 110 within the range provided by slot 126. Protrusion 128 both guides and limits the range of axial movement possible by distal end 123 of cross support 120 depending on the length of slot 126 provided. In one embodiment, protrusion 128 is disposed at about 90 degrees or perpendicular to each cross support 120 which may be substantially flattened in shape having a thickness (i.e. measured perpendicular to the plane of the paper in FIG. 4) that is less than the lateral width and length of each support.

Figure 2:
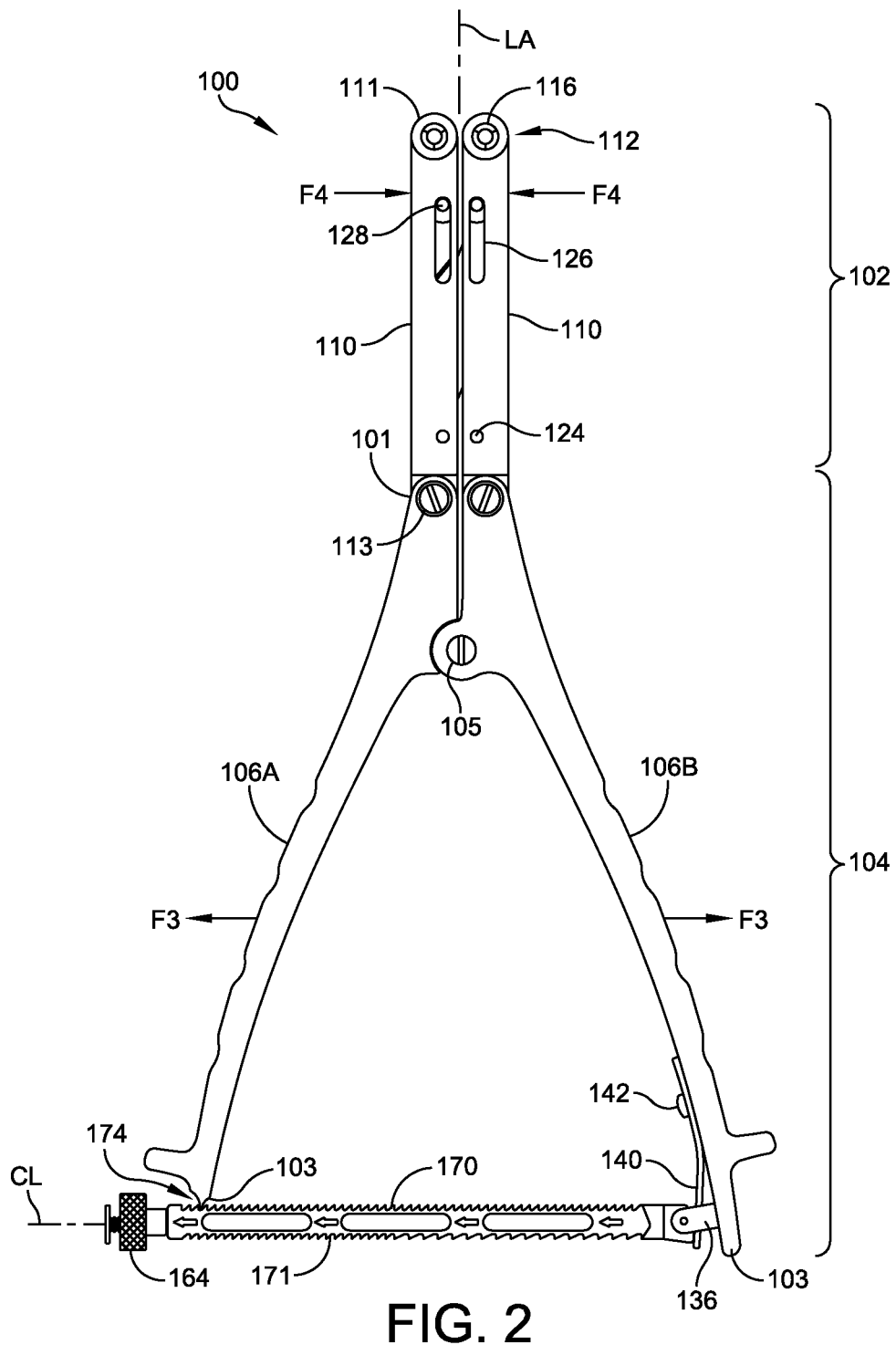
FIG. 2 is a front elevation view thereof showing working members in a closed position and handles in an open position.

Motion control brace 118 is expandable and contractable via movement of the lateral arms 110 together or apart, as shown for example in FIGS. 2 and 4. Ends 121 and 123 of each cross support 120 and varying portions of each support are received in passageway 119 in each lateral arm 110. The passageway 119 provides a space for allowing the control brace 118 to be almost completely nested inside arms 110 when the brace is fully contracted as shown in FIGS. 1 and 3. In FIG. 4, only the ends 121, 123 and adjacent portion of each cross support 120 are nested inside passageway 119 of the arms 110.

Motion control brace 118 advantageously restricts the movement of lateral arms 110 of working portion 102 to linear motion with respect to each other in a direction that is transverse to longitudinal axis. As further described herein, this embodiment ensures that spreading/distraction and compression of a bone joint occurs laterally across the joint and substantially parallel to the length of the mating bones (see, e.g. FIG. 1) to prevent oblique displacement of bone segments on opposing sides of the joint when tool 100 is engaged with the fixation elements which are properly positioned and implanted in the bone segments.

In operation, referring to the present embodiment shown in FIGS. 1-4, lateral arms 110 are moveable together relative to one another in a closing or inward compressing direction toward each other (see, e.g. FIGS. 2 and 3) and an opposing opening or outward distraction direction apart or away from each other (see, e.g. FIG. 4). During this closing or converging motion and opening or diverging motion, arms 110 and concomitantly their respective opposing faces or surfaces on the inside of each arm remain substantially parallel in alignment to each other in one embodiment as shown.

Referring to FIGS. 1-4, proximal ends 114 of lateral arms 110 are pivotally connected to distal ends 101 of handles 106A, 106B of the operating portion 104 via pivots 113 which in some embodiments may be fasteners or pins (not shown). In one, the connection may include a tongue 115 formed on arms 110 disposed between a pair of spaced apart ears 117 formed on handles 106A, 106B (see FIG. 1), or vice versa. Handles 106 are laterally disposed in relation to each other and pivotally connected via pivot 105 which may be a fastener or pin (not shown). In one embodiment, pivot 105 is disposed between handles 106A, 106B and disposed closer to distal ends 101 of handles 106A, 106B than proximal ends 103. Handles 106A, 106B are configured for opening and closing movement with respect to each other from an open operating position shown in FIGS. 1-3 to a closed operating position shown in FIG. 4. The operating portion 104 is configured so that moving the handles 106A, 106B apart in an opening direction moves the lateral arms 110 together in a closing compression direction, and moving the handles together in a closing direction handles moves the lateral arms apart in an opening distraction direction.

In one embodiment, referring to FIGS. 1-4, operating portion 104 has a distal portion 107 defined between pivot 105 and distal ends 104 and a proximal portion 107 defined between pivot 105 and proximal ends 103. Moving operating handles 106A, 106B between the open operating position (see, e.g. FIGS. 1-3) and closed operating position (see, e.g. FIG. 4) moves distal ends 104 together and apart respectively, which in turn concomitantly moves lateral arms 110 together and apart. Due to operation and the location of the pivot 105, the proximal ends 103 of handles 106A, 106B moves in an opposite lateral or transverse direction than distal ends 101 when the handles are squeezed close or pulled part by the user.

FIGS. 5-11 show proximal ends 103 of operating portion 104 and toothed ratchet member 130 in closer detail. Ratchet member 130 has one end 132 pivotally connected to proximal end 103 of one handle 106B and an opposing free end 134 disposed near and engageable with proximal end 103 of the other opposing handle 106A.

Toothed ratchet member 130 includes hollow outer toothed ratchet bar 150 and inner control rod 160 disposed within an axially elongated cavity 151 (see FIG. 6) in the ratchet bar. In one embodiment, ratchet bar 150 is both axially movable on the control rod 160 and rotatably movable with respect to the control rod without rotating the control rod for changing the position of the ratchet bar from a distraction operating position or mode to a compression operating position or mode, as further described herein. Control rod 160 is axially concentrically aligned with the centerline CL of the ratchet bar 150 in one embodiment as shown. Both ratchet bar 150 and control rod 160 each have a greater length than width, and are generally oriented transverse to the longitudinal axis of tool 100.

Figure 6:
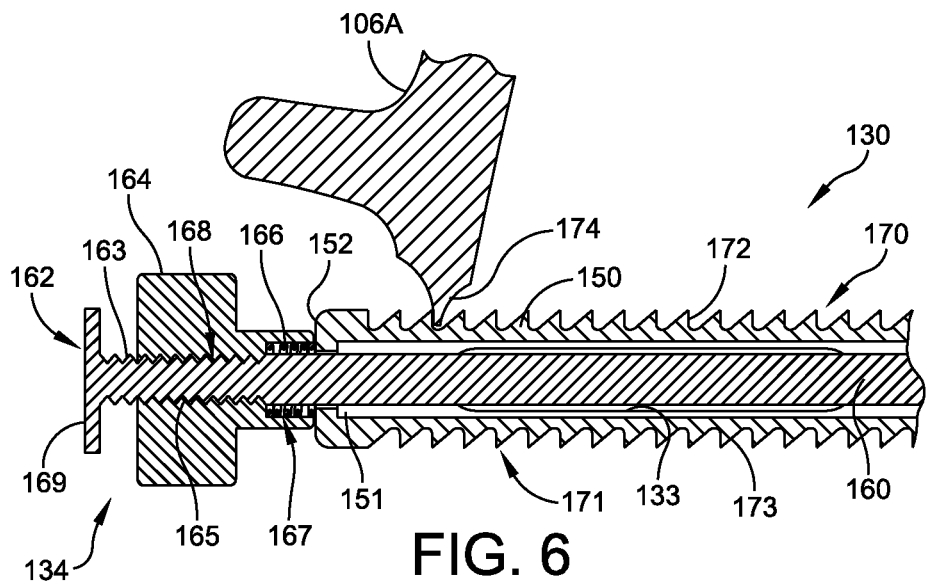
FIG. 6 is an enlarged cross-sectional side view of the lower left portion of the tool (with reference to FIG. 1) with locking knob in a blocking operating position.
Figure 7:
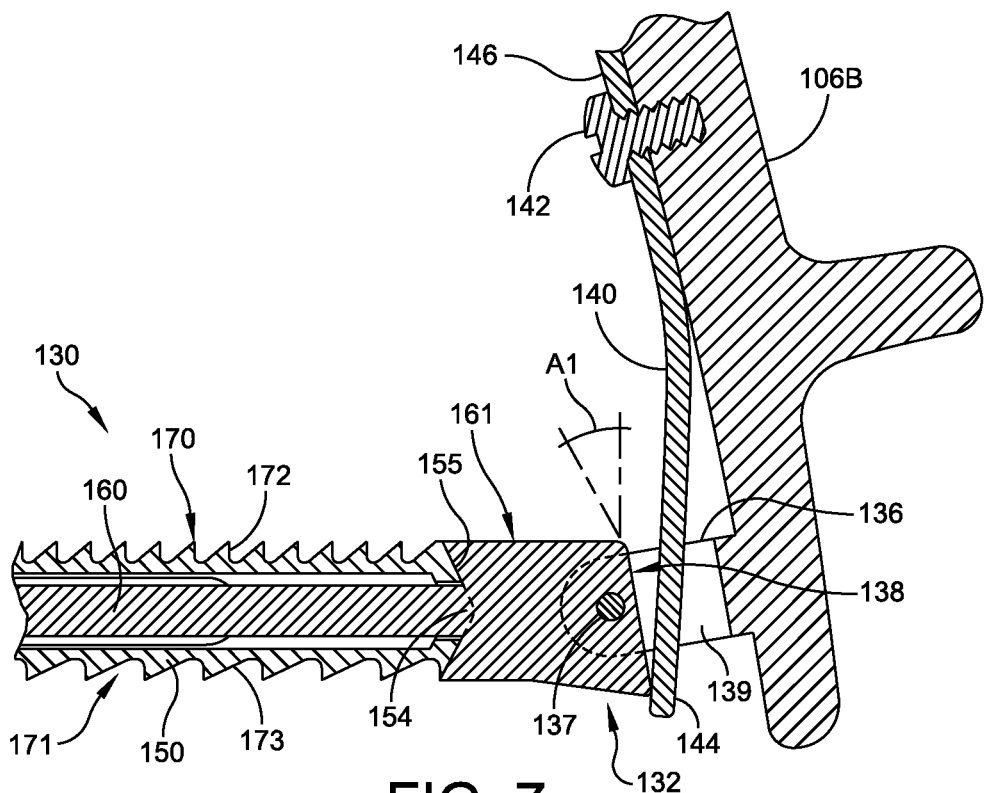
FIG. 7 is an enlarged cross-sectional side view of the lower right portion of the tool (with reference to FIG. 1) with the anti-rotation projection on ratchet member in a locked operating position.

Referring initially to FIGS. 6 and 7, control rod 160 is elongated having a circular cross-sectional shape (see FIG. 12) and includes a first end 161 coupled to handle 106B and second end 162. In one embodiment, end 161 is enlarged in size with respect to portions of control rod 160 disposed between the ends and is configured as a rectilinear or block-shaped tab that is insertable between spaced apart ears 139 of a mounting protrusion 136 disposed on handle 106B. In one embodiment, tabular shaped end 161 is cross pinned via pin 137 to ears 139 of protrusion 136 as shown for pivotal upward/downward movement of the control rod 160 and concomitantly ratchet member 130 with respect to handle 106B.

In one embodiment, tabular end 161 may include an angled end surface 138 disposed at an angle A1 to the top/bottom surfaces of the end as shown in FIG. 7. End surface 138 is acted on by an engaging biasing member 140 such as without limitation a flat spring as shown in some embodiments. Other suitable spring types and shapes may be used. Spring 140 is mounted to handle 106B via a fastening member 142 which may be a threaded fastener (shown) or alternatively a pin (not shown) in other embodiments. Fastening member 142 may be disposed near an upper distal end 146 of the spring 140 which has an opposite proximal end 144 that acts laterally against end surface 138 of control rod 160 so that the opposing end 162 (and ratchet member 130) is biased and urged in an upward generally longitudinal direction toward and abuttingly against the end 103 of opposing handle 106A (see directional arrow FIG. 5). Spring 140, which is normally flat in configuration, is pre-tensioned and flexed into a slightly bent configuration when mounted to handle 106 as shown due to combination of the outwardly flared shape of the handle and angled end surface 132 of ratchet bar 130. In one embodiment, proximal end 144 of spring 140 is received between ears 139 of protrusion 136 and captured between end surface 138 and handle 106B (see, e.g. FIGS. 5 and 7).

Figure 8:
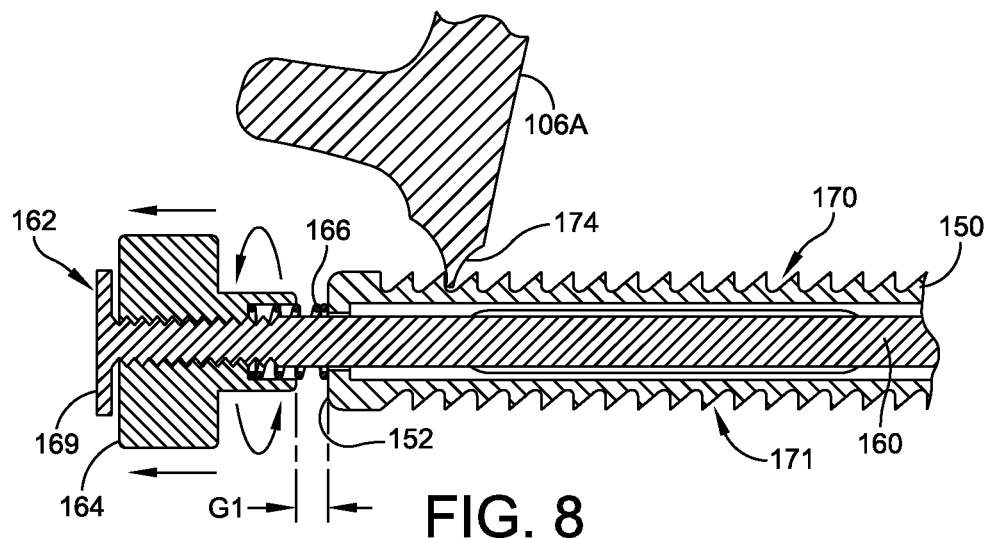
FIG. 8 is an enlarged cross-sectional side view of the lower left portion of the tool (with reference to FIG. 1) with locking knob in an unblocking operating position.

The opposite free end 162 of control rod 160 has an externally threaded portion 163 as shown in FIGS. 6 and 8. An internally threaded locking knob 164 threadably and rotatably engages threaded portion 163 and is axially movable in position on control rod 160 in two different opposite axial directions upon respectively rotating the knob in opposing rotational directions (compare FIGS. 6 and 8). Locking knob 164 includes an axially extending through passageway 168 of which at least part is a threaded portion 165 to engage threaded portion 163 of control rod 160. A cavity 167 is formed in one end of the knob 164 proximate to handle 106B which is configured to hold a spring 166 that acts between the knob and end 152 of ratchet bar 150 to bias the ratchet bar towards handle 106B. In one embodiment, spring 166 may be a helical spring; however, other suitable types of springs may be used. An end flange 169 is disposed on end 162 of control rod 160 to prevent the locking knob 164 from rotating off the end of the rod.

Locking knob 164 has an axial range of movement on control rod 160 from a first blocking position abuttingly engaged with ratchet bar 150 (see FIG. 6) to a second unblocking position abuttingly engaged with or proximate to flange 169 (see FIG. 8). Knob 164 is axially moveable between these positions by rotating or turning the knob in two different opposing directions. In some embodiments, as shown, locking knob 164 may have an outer knurled or other textured surface to facilitate gripping and turning the knob particularly when wearing surgical gloves.

Referring to FIGS. 5-12, ratchet bar 150 is elongated having a generally rectilinear cross-sectional shape including a opposing lateral sides 156, a top side 157, and a bottom side 158 (see FIG. 12). Ratchet bar 150 further includes a first end 153 slidably and abuttingly engageable with tabular end 161 of control rod 160 and second end 152 slidably and abutting engageable with locking knob 164. Ends 152 and 153 of the ratchet bar 150 each defines an opening that communicate with cavity 151 to allow the ratchet bar to be slid axially along the control rod 160.

Figure 9:
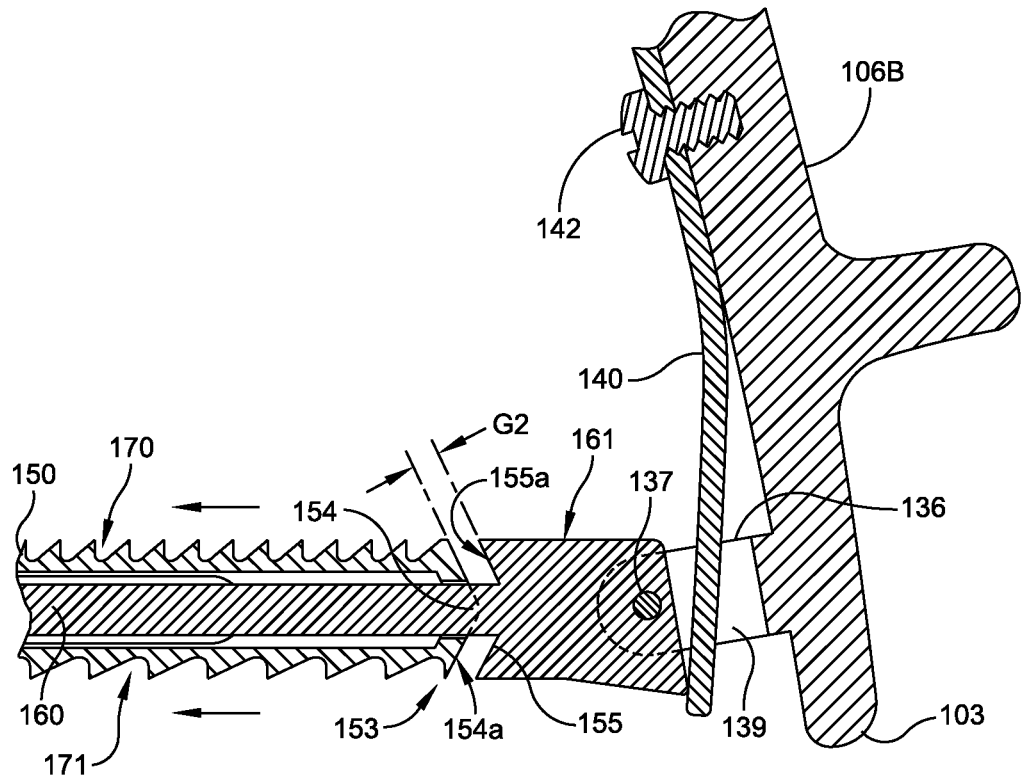
FIG. 9 is an enlarged cross-sectional side view of the lower right portion of the tool (with reference to FIG. 1) with the anti-rotation projection on ratchet member in an unlocked operating position allowing axial rotation of the ratchet member.

Ratchet bar end 153 and control rod tabular end 161 are mutually and complementary configured to provide an anti-rotation feature for the ratchet bar 150 wherein the ratchet bar is not rotatable on control rod 160 when ends 153 and 161 are engaged. In one possible embodiment, as shown in FIGS. 7 and 9, end 153 of ratchet bar 150 defines a V-shaped locking projection 154 and end 161 of control rod 160 defines a mating V-shaped locking recess 155 into which the projection is axially insertable and engageable to prevent rotation of the ratchet bar with respect to the control rod. Mating angled surfaces 154a and 155a of the ratchet bar 160 and control rod 160 respectively prevent twisting or rotation of the ratchet bar thereby defining a locked position. In other possible embodiments, tabular end 161 of control rod 160 may alternatively be provided with a V-shaped projection and end 153 of ratchet bar 150 may be provided with a V-shaped recess instead. Either arrangement may be used.

It will be appreciated that numerous other possible combinations of complementary configured mating projection and recess shapes may alternatively be used beyond just V-shapes so long as ratchet bar 150 is not rotatable when ends 153 and 161 are mutually engaged.

Figure 5:
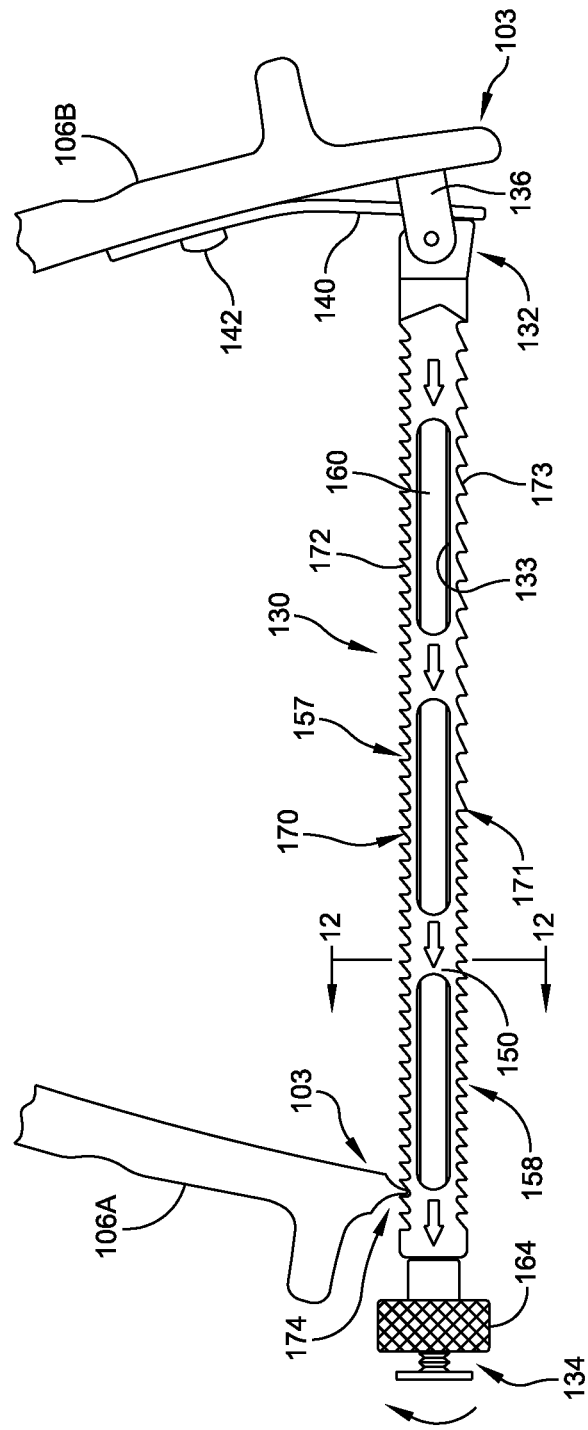
FIG. 5 is an enlarged front view of the proximal ends of the handles and tooth ratchet member of FIG. 1.

In some embodiments, axially elongated slot-shaped windows 133 may be provided in lateral sides 156 of ratchet bar 150 lighten the weight of surgical tool 100 (see, e.g. FIGS. 5 and 6).

With continuing reference to FIGS. 5-12, ratchet bar 150 includes at least a pair of tooth racks 170, 171 disposed on the sides of the ratchet bar. In one embodiment, tooth racks 170, 171 are arranged 180 degrees apart on opposite sides of the ratchet bar. In one embodiment, as shown, tooth rack 170 may be disposed on the top side 157 of ratchet bar 150 and tooth rack 171 may be disposed on the bottom side 158. Tooth rack 170 defines a plurality of axially arranged ratchet teeth 172 angled in a first axial direction or orientation (see, e.g. FIG. 6). In this embodiment, each tooth 172 comprises a vertical abutment surface and an angled or sloped sliding surface which faces towards handle 106A (i.e. towards the left in FIG. 6). Tooth rack 171 defines a plurality of axially arranged ratchet teeth 173 angled in a second opposite axial direction or orientation to ratchet teeth 172 (see, e.g. FIG. 6). In this embodiment, each tooth 173 comprises a vertical abutment surface and an angled or sloped sliding surface which faces towards handle 106B (i.e. towards the right in FIG. 6).

Tooth racks 170, 171 are configured to selectively engage a pawl 174 disposed on end 103 of handle 106A (see, e.g. FIGS. 5-11). Pawl 174 is configured with a convex pointed free end that is positioned to both slidably and abuttingly engage tooth racks 170, 171 in a ratcheting manner wherein depending on which tooth rack is presented to and engaged with pawl, the pawl is allowed to move in a single axial direction towards either handle 106A or 106B only as further described herein. Either tooth rack 170 or 171 may be selectively engaged with pawl 174 by rotating the ratchet bar 150 between a compression operating position or a distraction operating position. The upwards or top facing tooth rack 170 or 171 may be considered in an active ratcheting position whereas the downwards or bottom facing tooth rack may be considered in an inactive position.

Exemplary and non-limiting methods for operating the tool 100 and changing operational modes between a distraction mode and compression mode will now be described.

FIGS. 2 and 5-7 show tool 100 in a distraction operating mode. Although the method will now be described for convenience only with reference to distraction/compression of a bone joint (e.g. ankle, knee, etc.), the tool 100 may be used in other applications where distraction and compression of portions of one or more bones may be desired such as in fracture fixation.

Initially, the user who may be a surgeon secures the distal ends 111 to bone fixation elements 200 such as K-wires already mounted in bone on opposing sides of a closed joint in normal position as shown in FIG. 1. In embodiment of surgical tool 100 provided with locking members 111, the K-wires are clamped to the distal end 112 of tool 100 by tightening the locking members in a manner already described herein with respect to operation of the collet device. In alternative embodiments, the surgeon might choose to first put one K-wire into the bone and clamp distal end 112 thereto using one locking member 111, and then use the remaining open hole 116 on the other locking member 111 as a drill guide for inserting the second K-wire into the adjacent bone. In either case, the joint is now ready to be distracted or opened to provide access to interior portions of the bone joint such as to repair or remove cartilage in some possible applications. The locking knob 164 is in the blocking position, shown for example in FIGS. 5 and 6, wherein the ratchet bar 150 cannot be axially moved out of the locked position also shown in FIGS. 5 and 6.

As more clearly shown in FIGS. 5 and 6 in greater detail, tooth rack 170 is on top of ratchet bar 150 in the active position engageable with pawl 174 and tooth rack 171 is on bottom and in the inactive position not engageable with the pawl. The angled surfaces of the teeth 172 are facing towards handle 106A, meaning that the pawl 174 can ride on and slide over the teeth in a first axial direction towards handle 106B when the handles are squeezed together with inward force F1 in a closing motion as shown in FIG. 4. The lateral arms 110 connected to distal ends 101 of the handles simultaneously move apart with a force F2 for distraction of the bone joint via engagement with fixation elements 200 secured in the bone on opposite sides of the joint. A distraction position of tool 100 is shown in FIG. 4. It should be noted that the pawl 174 is prevented from moving in a second opposite axial direction towards handle 106A by engagement with the vertical abutment surface of the teeth 173 in the usual one-way ratcheting manner.

After the surgeon completes the procedure on the joint, the joint is next reclosed or compressed. Heretofore, it was necessary to uncouple and completely remove a separate distraction tool from the bone used to open the joint so that a different compression tool could be mounted to the bone fixation elements to then perform compression of the joint. This procedure is cumbersome and prolongs the duration of operating procedure. Advantageously, in embodiments according to the present disclosure, the surgeon can leave surgical tool 100 in place and coupled to the bone, and merely switch operating modes between distraction and compression to complete both opening and closure of the bone joint.

The method for switching operating modes of tool 100 will now be described. Referring to FIG. 8, the method starts with first rotating and unscrewing the locking knob 164 which is initially in the blocking position shown in FIG. 6. This causes the knob to travel axially towards handle 106A (see directional arrows). Spring 166, previously fully compressed as shown in FIG. 6, gradually expands with movement of the knob towards handle 106A as can be seen in FIG. 8. The knob 164 can be rotated towards flanged end 162 of control rod 160 for an axial distance until one end of the knob abuts flange 169. Knob 164 is now in the unblocking position shown in FIG. 8 allowing axial movement of the ratchet bar 150 with respect to the control rod 160 as further described herein.

It should be noted in FIG. 8 that a gap G1 is formed between end 152 of ratchet bar 150 and the end of knob 164 opposite that abutting flanged end 162 of control rod 160. Spring 166, acting on end 152 of ratchet bar 150, urges opposite end 153 of the ratchet bar against tabular end 161 of control rod 160, wherein mating locking angled surfaces 154a and 155a of the ratchet bar 160 and control rod 160 are mutually engaged as shown in FIG. 7.

Next, with gap G1 being formed as shown in FIG. 8, the surgeon axially slides ratchet bar 150 towards handle 106A as illustrated in FIG. 9 (see directional arrows) from the locked position (see FIG. 7) to the unlocked position (see FIG. 9). This compresses spring 166 with end 152 of the ratchet bar 150, thereby closing gap G1 and forming a second gap G2 at the opposite end 153 between angled surfaces 154a and 155b as shown.

Figure 10:
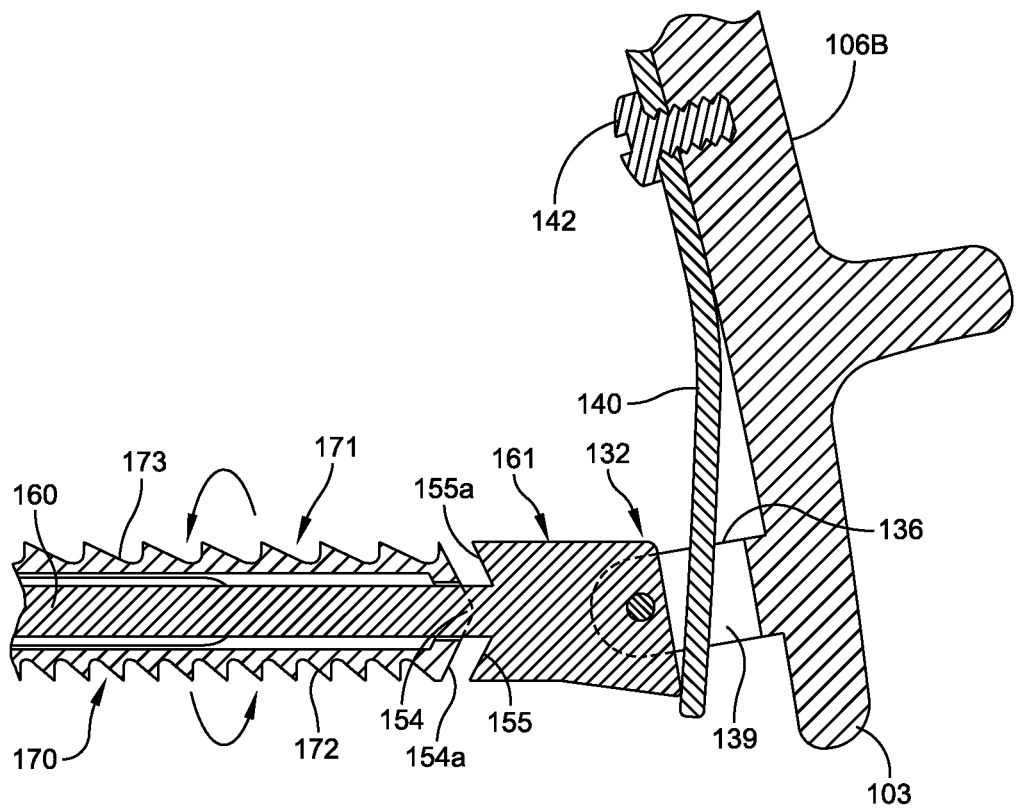
FIG. 10 is an enlarged cross-section side view thereof showing rotation of the ratchet member.

With the creation of gap G2, the surgeon next axially rotates ratchet bar 150 in relation to the control rod 160 (and handles 106A, 106B). The control rod 160 remains in a stationary fixed rotational position during rotation of the ratchet bar 150 because the control rod end 161 is pinned to protrusion 136 on handle 106B. In one embodiment, the ratchet bar 150 is rotated 180 degrees. Rotation of the ratchet bar 150 transposes tooth rack 170 previously on top of ratchet bar 150 in position with tooth rack 171 which is now presented to pawl 174, thereby switching operating modes of tool 100 from distraction to compression as shown in FIG. 10 (see directional arrows). Since the angled surfaces of teeth 173 faced towards handle 106B now, pawl 174 can axially move only towards handle 106A when the handles are pulled apart with a force F3 to compress the bone joint. In order to provide sufficient clearance between the pawl 174 and tooth rack 170 before rotating the ratchet bar 150, the end 134 of the ratchet member 130 may first be pulled downward and pivoted about pin 137 on handle 106B as shown in FIG. 11 (see directional arrows) against the upward biasing force of biasing member 140 thereby further compressing the spring. This will completely disengage the tooth rack 170 from pawl 174.

After tooth rack 171 is rotated to the top active position, ratchet bar 150 is released. Spring 166 urges and returns the ratchet bar 150 towards handle 106B thereby engaging again angled locking surfaces 154a and 155a (see, e.g. FIG. 11) to prevent rotation of the ratchet bar. Locking knob 164 is then rotated in an opposite direction from before thereby axially moving the knob from the unblocking position (see FIG. 8) to the blocking position (see FIG. 6). Upon pulling the handles 106A, 106b apart with force F3, the lateral arms 110 connected to distal ends 101 of the handles simultaneously move together with a force F4 for compression of the bone joint via engagement with fixation elements 200 secured in the bone on opposite sides of the joint. A compression position of tool 100 is shown in FIGS. 2 and 3. It should be noted that the pawl 174 is prevented from moving in an axial direction towards handle 106B by engagement with the vertical abutment surface of the teeth 173 in the usual one-way ratcheting manner.

Surgical tool 100 may be made of any suitable surgical grade materials including metals, non-metals, and combinations thereof for various components. In one embodiment, tool 100 is made of stainless steel. Biasing members 140 and 166 may be made of any suitable spring steel approved for surgical device applications.

Figure 14:
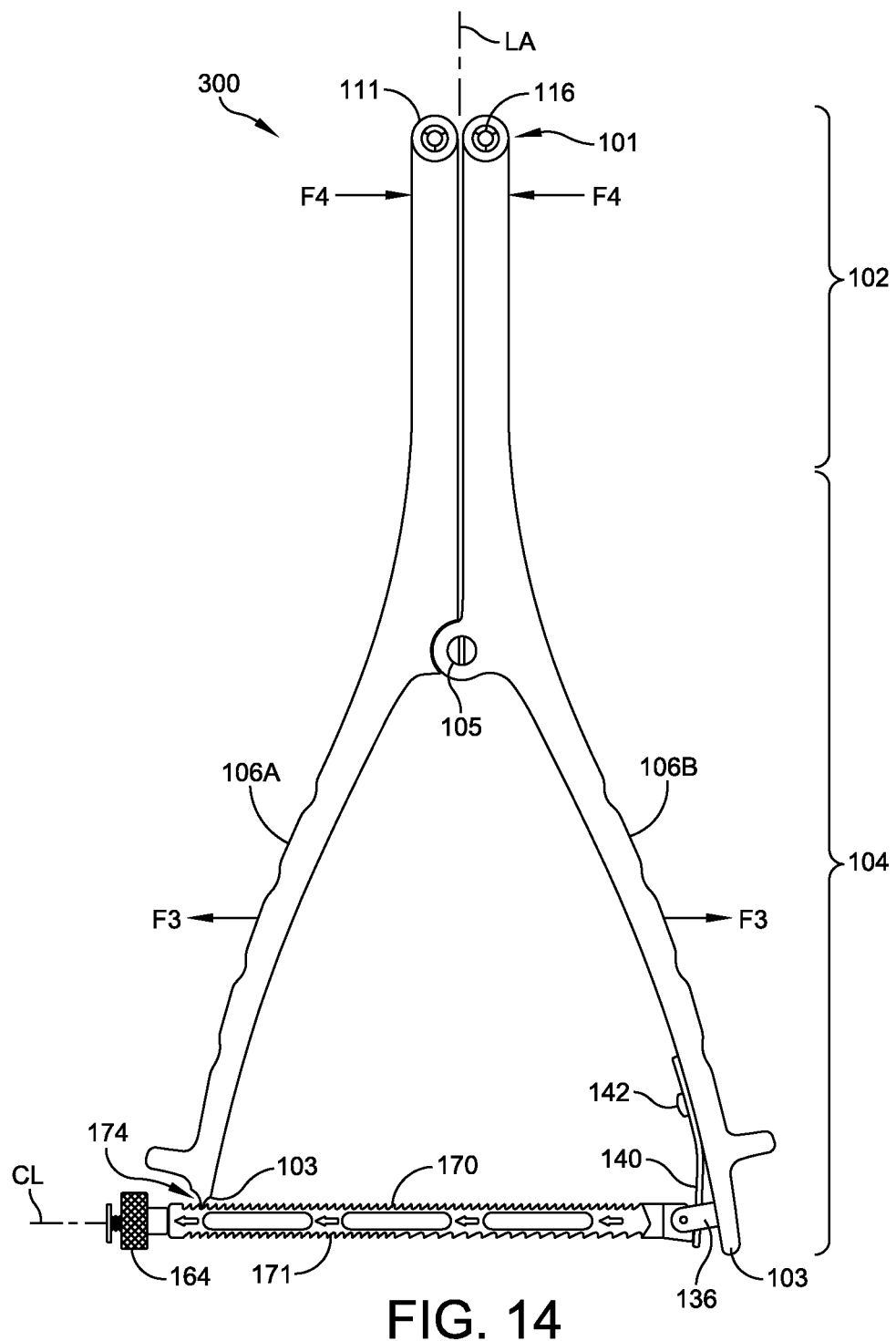
FIG. 14 is a front elevation view of an alternative embodiment of an improved surgical tool configured for compression and distraction operation.

FIG. 14 shows an alternative embodiment of a combined compression-distraction surgical tool 300 having a single pivot 105 that pivotally connects opposing handles 106A and 106B. The construction and arrangement of the elements of tool 300 is generally similar to surgical tool 100 already described herein. In tool 300, however, distal working portion 102 of tool 300 is defined by rigid portions of the distal ends 101 of the handles 106A, 106B lying above pivot 105 which are each constructed as an integral unitary structural part of the lower portions of each handle, as opposed to separate arms 111 each pivotally connected to distal ends of handles 106A, 106B (see, e.g. FIG. 1). In surgical tool 300, the working distal ends 112 of the tool configured to engage bone fasteners are instead defined by the distal ends 101 of handles 106A, 106B themselves which are extended in length and configured to engage a bone fastener. The distal ends 101 may therefore include cylindrical locking members 111 that define holes 116 to clampingly engage bone fasteners such as K-wires, or alternatively plain holes 116 are defined in distal ends of the handles for non-clamping engagement with the fasteners. In operation, the distal ends 101 and holes 116 therein of tool 300 will travel in a slightly arcuate path with respect to each other and pivot 105 upon opening and closing the handles, whereas the distal ends 112 of arms 110 will travel in a substantially linear path with respect to each other and pivot 105 due to motion control brace 120 (see FIGS. 3 and 4). Accordingly, surgical tool 100 provides substantially linear or straight line separation of a bone joint which in some surgical situations may be desirable.

The operating mode of surgical tool 300 can be switched between compression and distraction in essentially the same manner as tool 100 using toothed ratchet member 130, as previously described herein.

Although the surgical device and method have been described in terms of exemplary embodiments, they are not limited thereto. Rather, the appended claims should be construed broadly, to include other variants and embodiments of the surgical device and method, which may be made by those skilled in the art without departing from the scope and range of equivalents of the device and method.

What is claimed is:

1. A surgical tool comprising:
    a body including a distal working portion and a proximal operating portion pivotally coupled to the working portion;
    the working portion including a pair of elongated working members each having a distal end configured for engaging a fixation element securable to a bone segment, the working members movably coupled together and configured for motion in an opening distraction direction and a closing compression direction with respect to each other;
    the operating portion including a pair of elongated handles pivotally coupled together and configured for opening and closing movement with respect to each other, the operating portion being configured so that moving the handles apart in an opening direction moves the working members together in the closing compression direction, and moving the handles together in a closing direction handles moves the working members apart in the opening distraction direction;
    an elongated toothed ratchet member arranged across the handles and pivotally coupled to one of the handles, the ratchet member comprises an outer ratchet bar and an inner control rod disposed inside an axially elongated cavity formed in the ratchet bar, the ratchet bar being slidable between unlocked and locked positions with respect to the control rod, the ratchet member being engageable with a pawl disposed on the other handle, the ratchet member being rotatable between two different operating positions;
    wherein when the ratchet member is in a first operating position engaged with the pawl, the handles are movable in the closing direction and prevented from movement in the opening direction by the ratchet bar, and
    wherein when the ratchet member is in a second operating position engaged with the pawl, the handles are movable in the opening direction and prevented from movement in the closing direction by the ratchet bar.

2. The surgical tool of claim 1, wherein the ratchet member includes first and second tooth racks disposed on opposite sides of the ratchet member, the tooth racks being selectively and alternatingly engageable with the pawl by rotating the ratchet member between the first and second operating positions.

3. The surgical tool of claim 1 further comprising a locking knob rotatably disposed on the control rod, the knob being selectively engageable with one end of the ratchet bar to prevent sliding the ratchet bar on the control rod.

4. The surgical tool of claim 1 wherein one of the ratchet bar and control rod includes a locking projection engageable with a locking recess disposed on the other remaining one of the ratchet bar and control rod, the projection and recess being mutually configured to prevent rotation of the ratchet bar with respect to the control rod when engaged.

5. The surgical tool of claim 4, further comprising a spring acting between the locking knob and ratchet bar, the spring operable to bias the locking projection and recess into engagement.

6. The surgical tool of claim 1, further comprising a biasing member attached to one of the handles and urging one end of the ratchet member against the pawl.

7. The surgical tool of claim 1, further comprising a motion control brace coupling the working members together, the brace being operable to maintain the working members in substantially parallel relationship to each other when moving between the opening distraction direction and the closing compression direction.

8. The surgical tool of claim 1, wherein the ratchet member includes a first tooth rack comprising a plurality of teeth angled in a first direction and a second gear rack comprising a plurality of teeth angled in a second direction opposite the first direction.

* * * * *